United States Patent [19]
Eckhouse et al.

[11] Patent Number: 5,776,175
[45] Date of Patent: Jul. 7, 1998

[54] METHOD AND APPARATUS FOR TREATMENT OF CANCER USING PULSED ELECTROMAGNETIC RADIATION

[75] Inventors: Shimon Eckhouse; Michael Kreindel, both of Haifa, Israel

[73] Assignee: ESC Medical Systems Ltd., Yokneam, Israel

[21] Appl. No.: 536,985

[22] Filed: Sep. 29, 1995

[51] Int. Cl.$^6$ .................................................. A61F 2/00
[52] U.S. Cl. ........................... 607/100; 606/3; 607/90
[58] Field of Search ........................ 128/898, 736, 128/897; 600/2, 3, 7; 606/3, 7, 15, 27–31; 607/100, 89–90, 101, 102

[56] References Cited

U.S. PATENT DOCUMENTS

| | | |
|---|---|---|
| 4,022,534 | 5/1977 | Kishner . |
| 4,298,005 | 11/1981 | Mutzhas . |
| 4,608,978 | 9/1986 | Rohr . |
| 4,686,986 | 8/1987 | Fenyo et al. . |
| 4,757,431 | 7/1988 | Cross et al. . |
| 4,784,135 | 11/1988 | Blum et al. . |
| 4,829,262 | 5/1989 | Furumoto . |
| 4,862,886 | 9/1989 | Clarke et al. ..................... 606/15 X |
| 4,930,504 | 6/1990 | Diamantopoulos et al. . |
| 4,950,880 | 8/1990 | Hayner . |
| 5,161,526 | 11/1992 | Hellwing et al. . |
| 5,207,671 | 5/1993 | Franken et al. . |
| 5,217,455 | 6/1993 | Tan . |
| 5,226,430 | 7/1993 | Spears et al. ..................... 128/898 |
| 5,259,380 | 11/1993 | Mendes et al. . |
| 5,320,618 | 6/1994 | Gustafsson . |
| 5,344,418 | 9/1994 | Ghaffari . |
| 5,344,434 | 9/1994 | Talmore . |
| 5,368,031 | 11/1994 | Cling et al. ..................... 606/15 X |
| 5,386,837 | 2/1995 | Sterzer ............................ 128/898 |

FOREIGN PATENT DOCUMENTS

3906860-A1  9/1989  Germany .

OTHER PUBLICATIONS

Diffusion of Light in Turbid Material, A. Ishimaru, Applied Optics 1989, vol. 28, No. 12, pp. 2210–2215.
Role of Skin Optics in Diagnostic and Therapeutic Uses of Lasers, S. L. Jacques, Springer–Verlag, 1991, pp. 1–21.
Whole–Body Hyperthermia in Cancer Therapy: A Report of A Phase I–II Study, J. van der Zee, et al., Eur. J., Cancer Clinical Oncology, 1983, vol. 19, No. 9, pp. 1189–1200.
Relationship of Response to Transurethral Hyperthermia and Prostate Volume in BPH Patients, Z. Petrovich, F. Ameye, M. Pike, S. Boyd, L. Baert, Urology, 1992, vol. 40, No. 4, pp. 317–321.
Nd: YAG Laser–Induced Hyperthermia in A Mouse Tumor Model, S. M. Waldow, P. R. Morrison, L. I. Grossweiner, Lasers in Surgery and Medicine, 1988, vol. 8, No. 5, pp. 510–514.
Light and Electron Microscopic Analysis of Tattoos Treated by Q–Switched Ruby Laser, C. Taylor, R. R. Anderson, et al., J. of Investigative Dermatology, 1991, vol. 97, pp. 131–136.
Treatment of Benign Cutaneous Pigmented Lesions with the Candela 510 NM Pulsed Laser, Laser Med. and Surgery Abstracts, R. E. Fitzpatrick, et al., 1992, vol. 4S, p. 73.
Treatment of Benign Cutaneous Pigmented Lesions with the Candela 510 NM Pulsed Laser, Laser Med. and Surgery Abstracts, R. E. Fitzpatrick, et al., 1992, vol. 4S, p. 73.

*Primary Examiner*—John P. Lacyk
*Assistant Examiner*—Ryan Carter

[57] ABSTRACT

The invention includes a method for the hyperthermic treatment of tumors including the steps of providing a pulsed radiation output from a radiation source; and directing said pulsed radiation output toward a tumor. The invention further includes an apparatus for the treatment of tumors having a radiation source adapted to produce broad-band pulsed radiation output at least in the visible and near-infrared range of wavelengths, a delivery system proximal to the radiation source and adapted to focus and direct the pulsed radiation output to a dermal treatment site, and a filtering system adapted to restrict the pulsed radiation output to bands in the visible and near-infrared range of wavelengths.

11 Claims, 2 Drawing Sheets

METHOD AND APPARATUS FOR TREATMENT OF CANCER USING PULSED ELECTROMAGNETIC RADIATION

This invention relates to an apparatus and method for the treatment of tumors. More particularly, the invention relates to an apparatus for the irradiation of shallow tumors with pulsed electromagnetic radiation.

FIELD OF THE INVENTION

Several non-surgical methods are available for treatment of cancer, but all of them have disadvantages. Chemical therapy and photodynamic therapy are accompanied by the introduction of a toxic agent into the body. Electromagnetic radiation therapy using X-rays causes the destruction of healthy tissue due to X-rays ability to penetrate deeply into human tissue.

Another method, called hyperthermia, is used for tumor necrosis both by itself, and in combination with other methods of cancer treatment. The basic purpose of hyperthermia is to raise tumor temperature substantially above body normal temperature, to a temperature at which tumor cells are killed. The "selectivity" of hyperthermic therapeutic methods are the extent to which the tumors and not the surrounding healthy tissue is destroyed. Hyperthermic treatments have been employed for both whole body heating and for local heating of tumors. Local hyperthermia typically uses sources of electromagnetic radiation, focused on the tumor at frequencies that will heat tumor tissue and not the surrounding healthy tissue. Microwave, visible and infrared frequency ranges are commonly employed for this purpose.

Current hyperthermic methods have significant disadvantages. Treatment times are often long, on the order of an hour. Furthermore, the selectivity of the radiation is low, causing necrosis not only of tumor tissue, but of the healthy surrounding tissue as well.

Hyperthermia treatments using microwave radiation sources (typically radiating at about 915 MHz) have the disadvantage of deep non-tunable penetration (several centimeters) into the body as well as problems with focusing which cause low selectivity.

Nd:YAG laser radiation sources are used both by themselves and in combination with photodynamic therapy. One disadvantage of Nd:YAG laser when used for hyperthermia is its small spot size, on the order of 5 mm. A radiation source this small cannot easily heat large tumors, which may have a projected area of several square centimeters on the skin, resulting in extended treatment times. In addition, the Nd:YAG laser has other limitations relating to their continuous wave (CW) operating mode, and with their limited tunable range. It is clear that an improved apparatus and method for hyperthermia tumor treatment is desirable.

Pulsed radiation of a tumor using a light source would cause more efficient hyperthermia and necrosis than current methods provide. Furthermore, a radiation source capable of heating tissue in a short time interval, preferably between 41 and 45 degrees C., would reduce the treatment times currently required. Providing a radiation source with a broad controllable spectrum of radiation in the visible and near infrared regions would allow the penetration depth and the selectivity of the treatment to be more accurately controlled.

SUMMARY OF THE PRESENT INVENTION

The present invention is directed to a method for the hyperthermic treatment of tumors with electromagnetic radiation including the steps of providing a pulsed radiation output from a radiation source and directing said pulsed radiation output toward a tumor. The radiation may be developed over at least one continuous band of wavelengths, or be generated in the visible and near-infrared band, possibly in a continuous band between 600 and 1000 nm. In one embodiment, it may include the step of transmitting a broad radiation beam to a pigmented tumor, which might have a cross-sectional area of between 0.8 $cm^2$ and 500 $cm^2$. In another embodiment, it is possible to control the pulse-width of the pulsed radiation output, focus the radiation source for controlling the power density of the pulsed radiation output, or filter and control the spectrum of the pulsed radiation output. In particular, one may focus the pulsed radiation output to a beam having a cross-sectional area of greater than 0.8 $cm^2$. Alternatively, one may cut off the UV portion of the spectrum. A pulse width in the range of about 100 microseconds to 50 milliseconds may be provided, particularly, one having an energy density at the treatment area of at least 0.2 $W/cm^2$. Alternatively, energy densities of greater than 90 $J/cm^2$, 120 $J/cm^2$ per treatment may be provided at the treatment site. A pulse delay of greater than 100 milliseconds or less than 100 seconds may also be provided.

In another embodiment of the invention, an apparatus for the treatment of tumors is provided, including a radiation source producing pulsed radiation at least in the visible and near-infrared wavelengths, a delivery system near the radiation source for focusing and directing the radiation to a treatment site, and a filtering system restricting the radiation to visible and near-infrared wavelengths. Alternatively, the radiation source may produce pulsed radiation in a broad band, or over at least one continuous range of wavelengths. This may be focused in a beam of at least 0.8 $cm^2$. The radiation may be restricted to a band between 300 and 1000 nm, or may be UV blocked by a filter. The radiation pulses may have a duration of between 100 μsecs and 100 msecs, and may be spaced from 100 msecs to 100 secs apart. In addition, they may be delivered to the treatment area with a radiation density of greater than 0.2 $W/cm^2$, 90 $J/cm^2$, or 120 $J/cm^2$. The radiation may also be limited to a radiation density of less than 200 $J/cm^2$.

Other principal features and advantages of the invention will become apparent to those skilled in the art upon review of the following drawings, the detailed description and the appended claims.

Figure 1:
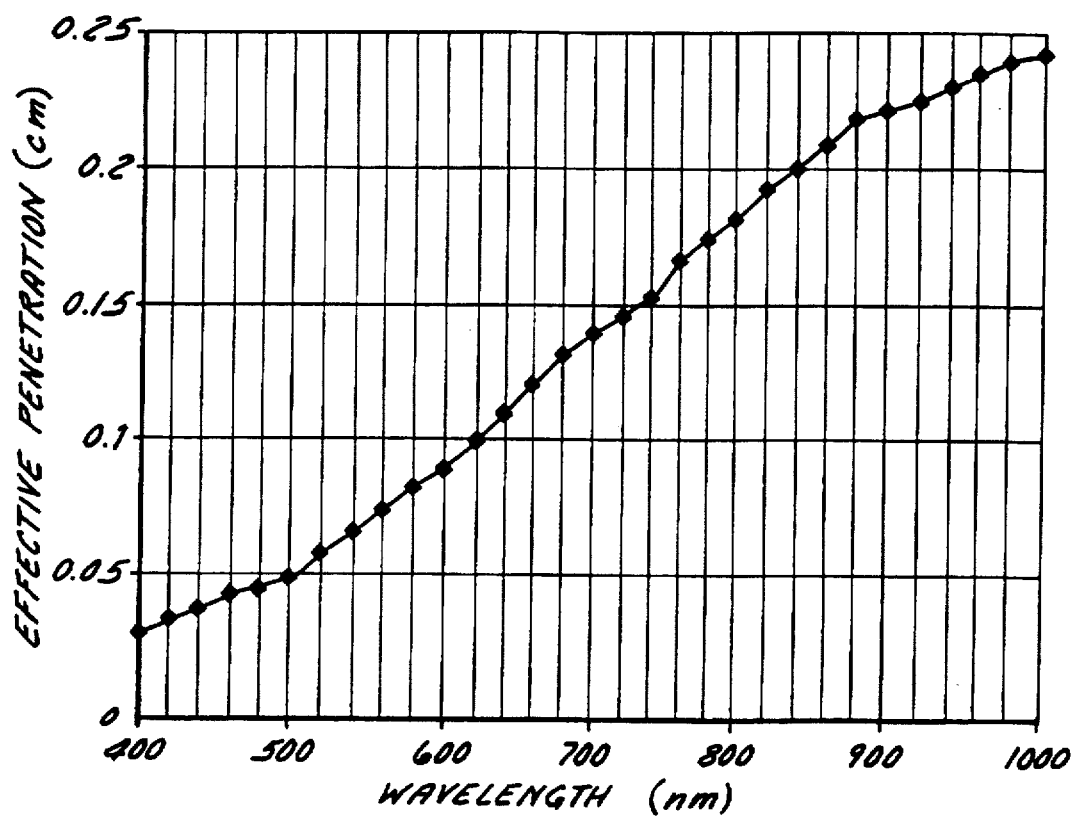
FIG. 1 is a graph of radiation tissue penetration versus radiation wavelength.

Before explaining at least one embodiment of the invention in detail it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION OF THE PREFERRED EMBODIMENTS

The present invention is directed to a method and apparatus for treating shallow tumors using pulsed radiation.

Treatment of such tumors is problematic, since the outer layers of skin must be penetrated and not harmed, yet the radiation must get to the underlying tumorous growth sufficient to heat the tumor and cause necrosis. The "effective penetration depth", d, of radiation is a measure of the radiation's ability to penetrate the skin and affect an underlying tumor. It is defined herein as the depth below the surface of the skin at which the radiation fluence reaches 1/e times the magnitude of the radiation fluence on the surface of the skin. Since the effective penetration depth varies with the wavelength of the impinging radiation, tumors at a particular depth can be targeted, and the overlying skin preserved, by selecting and applying particular wavelengths of radiation for tumors at a particular depth.

The effective penetration depth can be estimated by using the effective attenuation coefficient, $\mu_{eff}$, of the dermis, which takes into account the scattering and absorption of light in tissue. The relation of the effective penetration depth to the effective attenuation coefficient can be estimated as:

$$d = 1/\mu_{eff}$$

Following Jacques (S. L. Jacques, Role of Skin optics in Diagnostic and Therapeutic Uses of Lasers, "Lasers and Dermatology", Springer-Verlag, 1991, pp.1–21), the effective attenuation coefficient of the dermis can be expressed as follows:

$$\mu_{eff} = \{3\mu_a(\mu_a + \mu_s(1-g))\}^{1/2},$$

where $\mu_{eff}$=attenuation coefficient of dermis $\mu_a$=absorption coefficient of dermis $\mu_s$=scattering coefficient of dermis, and g=the anisotropy factor, defined as the average cosine of the scattering angle for one scattering event.

Using the above coefficients and factor, a chart has been made of the effective penetration depth in centimeters versus the wavelength of electromagnetic radiation impinging upon the skin. This chart is illustrated in FIG. 1. As FIG. 1 discloses, the effective penetration depth increases with increasing wavelength, and for wavelengths between 400 nm and 1000 nm varies between 0.03 cm and 0.25 cm. Radiation can penetrate as deeply as 2 mm with a radiation wavelength of 800 nm. The sensitivity of effective penetration depth to wavelength is clear from this chart. For example, d doubles when the wavelength of the impinging radiation increases by a mere 20% (500 to 600 nm). Because varying the applied radiation wavelength varies the depth of penetration of that radiation, one can control treatment depth by controlling the radiation wavelength.

Hyperthermic treatments also depend upon the length of time radiation is applied to the surface of the skin. The effective depth of tissue heating based on heat conducted from the surface depends upon the conductivity of the skin. The time t, required for a heat wave to penetrate to a depth d, below the surface of the skin can be expressed as:

$$t = d^2/a,$$

where a=the diffusivity of the skin (approximately $3 \times 10^{-7}$ m$^2$ sec$^{-1}$).

Thus, the depth of penetration can be controlled by controlling the time interval over which radiation is applied to the surface of the skin. For example, conducting heat from the surface of a skin throughout a shallow tumor with a thickness of about 1 cm requires about a 5 minute application of radiation to the surface of the skin.

These two modes of heating: conduction from the surface of the skin, and radiant penetration, can be tailored to specific tumors by varying the wavelength and the pulse duration.

A major limitation to the use of radiation sources for therapeutic treatment is the potential tissue damage. In order to radiate the tumor with the optimum wavelengths of radiation yet not burn tissue, a radiation source is preferably pulsed, thereby providing radiation at wavelengths sufficient to penetrate the tumor to an optimum depth, yet limiting the average energy density during a treatment and preventing the upper layers of the tumor from being overheated.

To provide for the treatment of a wide range of shallow tumors, the preferred energy density per pulse is between 0.1 and 10 Joules per square centimeter of tumor area. These pulses are preferably repeated at a rate of between 0.1 and 1 Hertz. The number of pulses for treating shallow tumors preferably ranges between 1 and 1000 pulses. To treat a wide range of tumor sizes, the radiation should be applied to an area of the skin ranging from 0.8 cm$^2$ to 500 cm$^2$.

Figure 2:
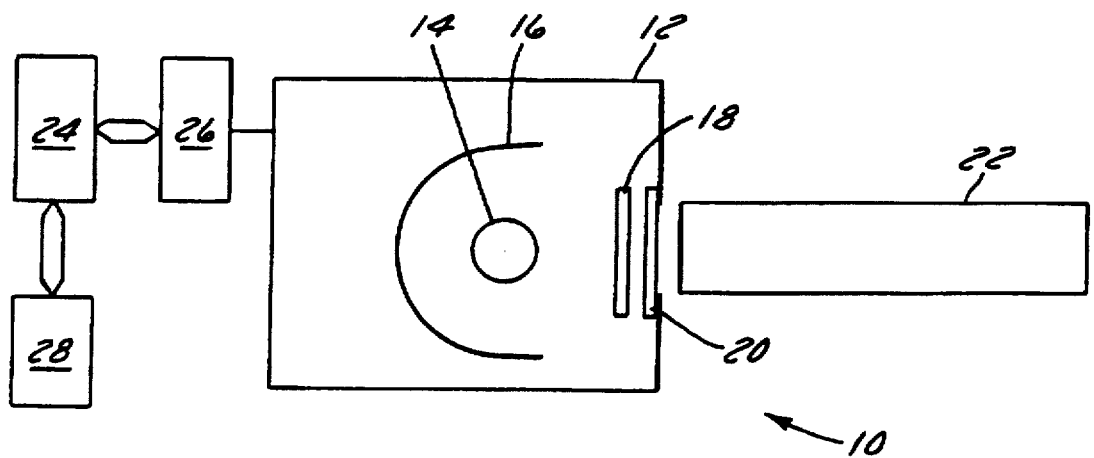
FIG. 2 is a cross-sectional view of tumor treatment device according the present invention.

It is clear from FIG. 1 that by irradiating a tumor with selected bands of radiation in the visible and near infrared regions, the tumor can be penetrated to a depth of between 0.05 and 0.25 cm and hyperthermically treated. FIG. 2 illustrates just such a tumor treatment apparatus 10, having a housing 12 that encloses a radiation source 14, and a reflector 16, and having an opening with a set of optical filters 18,20, and a delivery system 22. A processor 24 is provided to control radiation source 14 through lamp driver circuit 26, under the control of a program in memory 28.

Radiation source 14 is a flashlamp such as a gas filled linear flashlamp Model No. L5568 available from ILC. Typically, a flashlamp's energy is emitted as broad-band incoherent energy in the 300 to 1000 nm wavelength range, which, as FIG. 1 shows, is well-suited to penetrating tissue to a depth of several millimeters, and thus, for treating shallow tumors.

To treat a tumor, the radiation must be focused and delivered to the treatment site, and thus reflector 16 and delivery system 22 are provided. Reflector 16 gathers the radiation and directs it toward an opening in the housing. To effectively reflect radiation in the 300 to 1000 nm band, reflector 16 is preferably metallic, typically aluminum which is easily machinable and polishable, and has a very high reflectivity in the visible and near infrared ranges of the spectrum. Other bare or coated metals can also be used for this purpose.

Optical filters 18 and neutral density filters 20 are mounted in housing 12 and may be moved into the beam or out of the beam to control the spectrum and intensity of the light. The optical filters may include bandwidth and low cutoff filters in the visible and infrared portions of the spectrum. To limit skin damage, it is desirable to employ UV filters to block the UV portion of the spectrum, in particular, UV filters that cut off the spectral range below 510 nm. For deeper penetration it is preferable to use narrower bandwidth filters. Optical bandwidth filters and the cutoff filters are readily available commercially. Neutral density filters with varying degrees of filtration can be used to reduce the total fluence transmitted to the skin by blocking the transmission of radiation emitted by the radiation source to the treatment site.

The radiation is delivered to the treatment site by delivery system 22, typically an optical fiber or a quartz light guide, although it may be preferable to emit light directly from an opening in the housing. The delivery system should produce fluences on the skin of between 100 mJ/cm² to 10 J/cm².

Radiation source 14 is pulsed to provide control of the total fluence, and thus control of tumor and skin heating. To vary the fluence, the delay interval between pulses may be increased or decreased, preferably over a range of a hundred milliseconds to tens of seconds. In this manner, the tumor can be heated at a rate sufficient to allow skin penetration and tumor necrosis, yet not overheat tissue. Total fluence can also be controlled by varying the duration of each pulse over a range of between a hundred microseconds and tens of milliseconds, to vary the fluence per pulse from a hundred millijoules to tens of Joules using a flashtube. Total fluence can also be modified by varying the energy per pulse.

Effective penetration depth is dependent on the wavelength of radiation received at the surface of the skin. The present invention provides for changes in wavelength in several ways. Filter 18 can be a low-pass or band-pass filter, thereby blocking selected wavelengths of light. Varying the power per pulse will also vary the emission spectrum of the radiation source as well.

Processor 24 is provided to control the energy per pulse, the pulse repetition rate, pulse duration rate and the number of pulses per a single treatment. It is connected to radiation source 14 through a lamp driver circuit 26, which is capable of generating power sufficient to trigger radiation source 14. Processor 24 operates under the control of a program stored in memory circuit 28.

The present invention is well suited to treating tumors with a wide variety of sizes. For smaller tumors, a fiber optic delivery system is appropriate. By directing the radiation through a fiber to the treatment site, small tumors typically on the order of a millimeter or larger in breadth can be treated without endangering the surrounding tissue. Larger tumors, typically on the order of several square centimeters in projected area, can be treated using a delivery system, that focuses and applies the radiation to a wider treatment site, preferably radiating a 0.8 cm² area of the treatment site or larger. By applying the radiation over a larger area, for example 500 cm², even heating of large tumors can be achieved, reducing the chance of uneven tumor treatment and the risk of damaging tissue.

Figure 3:
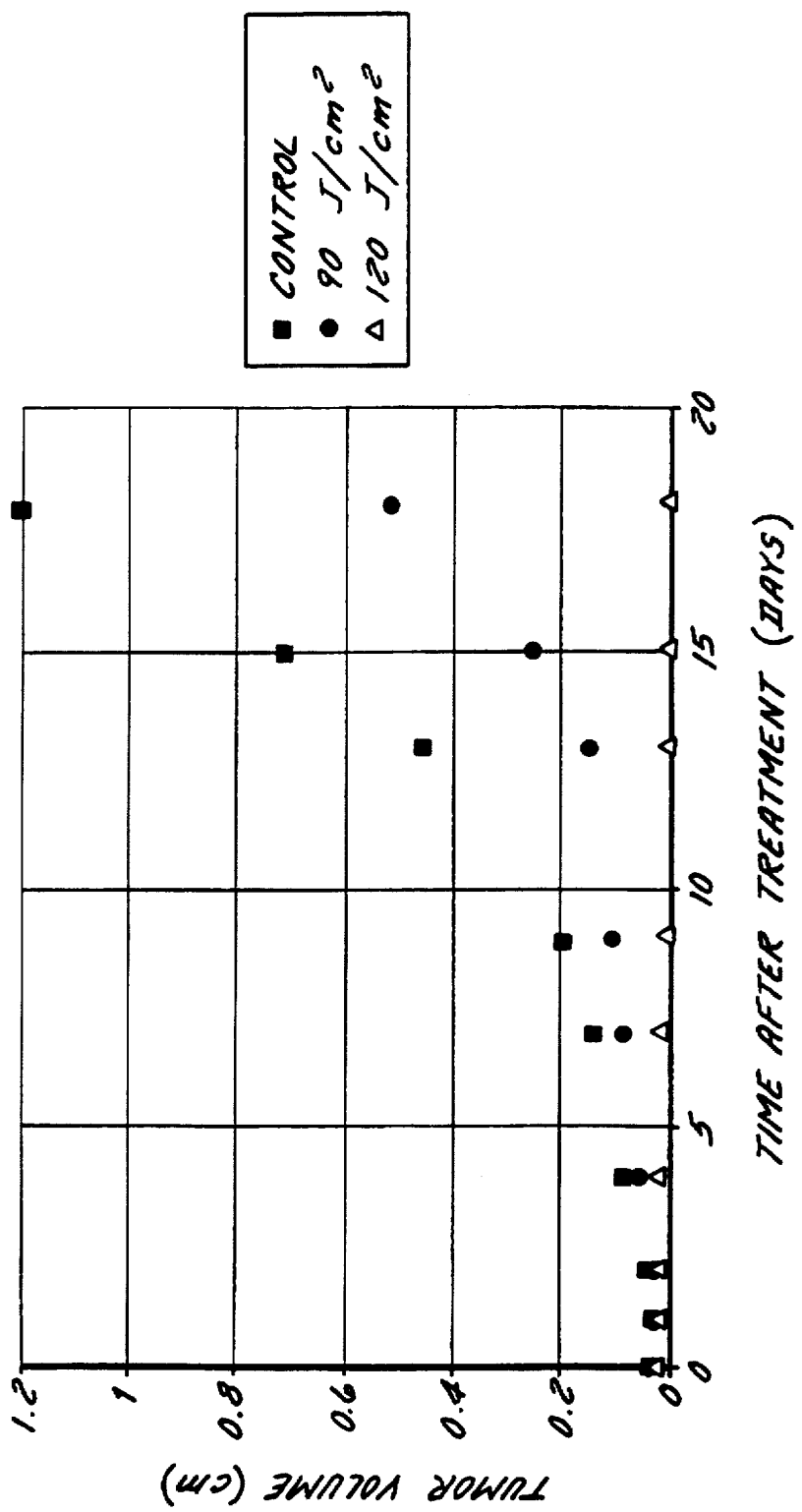
FIG. 3 is a graph of treatment results using the FIG. 2 tumor treatment device.

The present invention has been tested in animal trials and is effective for the treatment of tumors. FIG. 3 illustrates the inhibition of melanoma B16 growth in mice after irradiation in accordance with this invention. The FIG. 3 chart compares tumor volume versus time for three irradiation levels: a control level (0 J/cm²); 90 J/cm²; and 120 J/cm². Irradiation levels of 90 J/cm² clearly and significantly delay tumor growth, and an irradiation level of 120 J/cm² causes the affected tumor to shrink in size. Extrapolating from these tests, irradiation levels of 200 J/cm² are believed to provide therapeutic results. The tumor treatment apparatus in these tests applied broad-band radiation in the band from 600 nm to 1000 nm to the tumor. No apparent tumor response was observed for average radiation power densities below 0.2 W/cm².

Thus, it should be apparent that there has been provided in accordance with the present invention a method and apparatus for the hyperthermic treatment of tumors that fully satisfies the objectives and advantages set forth above. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

We claim:

1. A method for the hyperthermic treatment of tumors with electromagnetic radiation comprising the steps of:

providing pulsed radiation cutout from a radiation source;

directing the pulsed radiation output toward a tumor:

controlling the pulse-width of the pulsed radiation output;

focusing the radiation source for controlling the power density of the pulsed radiation output; and filtering and controlling the spectrum of the pulsed radiation output, wherein the step of providing a pulsed radiation output includes the step of generating the pulsed radiation output over at least one continuous band of wavelengths; and wherein said step of controlling the pulse width includes the step of providing a pulse width in the range of about 100 microseconds to 50 milliseconds with energy density of the pulsed radiation output at the treatment area of at least 0.2 W/cm²; and wherein the energy density of the pulsed radiation output at the treatment area is greater than 90 J/cm² per treatment.

2. The method of claim 1 wherein the energy density of the pulsed radiation output at the treatment area is greater than 120 J/cm² per treatment.

3. A method for the hyperthermic treatment of tumors with electromagnetic radiation comprising the steps of:

providing pulsed radiation output from a radiation source;

directing the pulsed radiation output toward a tumor;

controlling the pulse-width of the pulsed radiation output;

focusing the radiation source for controlling the power density of the pulsed radiation output; and filtering and controlling the spectrum of the pulsed radiation output, wherein the step of providing a pulsed radiation output includes the step of generating the pulsed radiation output over at least one continuous band of wavelengths; and wherein said step of controlling the pulse width includes the step of providing a pulse width in the range of about 100 microseconds to 50 milliseconds with energy density of the pulsed radiation output at the treatment area of at least 0.2 W/cm²; and further including the step of providing a pulse delay of greater than 100 milliseconds.

4. The method of claim 3 wherein the step of providing radiation delays includes the step of limiting the delay duration to less than 100 seconds.

5. An apparatus for the hyperthermic treatment of tumors comprising:

a radiation source adapted to produce pulsed radiation output at least in the visible and near-infrared range of wavelengths sufficient to heat the tumor to cause tumor cell necrosis;

a delivers system proximal to the radiation source and adapted to focus and direct the pulsed radiation output to a cancerous tumor at a dermal treatment site; and a filtering system adapted to restrict the pulsed radiation output to bands in the visible and near-infrared range of wavelengths wherein the filtering system includes a filter adapted to block UV wavelengths, and wherein the radiation source is adapted to produce said pulsed radiation output over at least one continuous band of wavelengths, and is adapted to provide a pulse duration between 100 microseconds and 100 milliseconds.

6. The apparatus of claim 5, wherein the pulsed radiation source is adapted to provide a pulse delay of between 100 milliseconds and 50 seconds between pulses.

7. The apparatus of claim 6, wherein the delivery system is adapted to deliver the pulsed radiation output to the dermal treatment site with a radiation density of greater than 0.2 W/cm$^2$.

8. The apparatus of claim 7, wherein the delivery system is adapted to deliver the pulsed radiation output to the dermal treatment site with a radiation density of greater than 90 J/cm$^2$.

9. The apparatus of claim 8, wherein the delivery system is adapted to deliver pulsed radiation output to the dermal treatment site with a radiation density of less than 200 J/cm$^2$.

10. The apparatus of claim 9, wherein the delivery system is adapted to deliver pulsed radiation output to the treatment area with a radiation density of greater than 120 J/cm$^2$.

11. The apparatus of claim 6 further including a processor adapted to control the pulse duration and pulse delay.

* * * * *

UNITED STATES PATENT AND TRADEMARK OFFICE
CERTIFICATE OF CORRECTION

PATENT NO. : 5,776,175
DATED : July 7, 1998
INVENTOR(S) : Shimon Eckhouse, et al It is certified that error appears in the above-identified patent and that said Letters Patent is hereby corrected as shown below:

Column 6, line 19, change "energy" to --power--.

Column 6, line 43, change "energy" to --power--.

Column 7, line 5, after "radiation" insert --power--.

Column 7, line 9, after "radiation" insert --energy--.

Column 8, line 2, after "radiation" insert --energy--.

Column 8, line 6, after "radiation" insert --energy--.

Column 2, line 18, change "energy" to --power--.

Column 2, line 38, after "radiation" insert --power--;

Column 2, line 38, before "90" insert --or energy density of greater than--.

Column 2, line 39, after "radiation" insert --energy--.

Column 5, line 48, last line before "levels" insert --energy density--.

UNITED STATES PATENT AND TRADEMARK OFFICE
CERTIFICATE OF CORRECTION

PATENT NO. : 5,776,175

DATED : July 7, 1998

INVENTOR(S) : Shimon Eckhouse, et al

It is certified that error appears in the above-identified patent and that said Letters Patent is hereby corrected as shown below:

Column 5, line 50, before "levels" insert --energy density--.

Column 5, line 51, before "level" insert --energy density--.

Signed and Sealed this

Ninth Day of February, 1999

Attest:

Attesting Officer

*Acting Commissioner of Patents and Trademarks*